US006741954B2

(12) United States Patent
Sonnenberg et al.

(10) Patent No.: US 6,741,954 B2
(45) Date of Patent: May 25, 2004

(54) SELECTION METHOD FOR ODORANTS

(75) Inventors: Steffen Sonnenberg, Holzminden (DE); Anja Finke, Holzminden (DE); Andreas Klamt, Leverkusen (DE); John Lohrenz, Leverkusen (DE); Thorsten Bürger, Köln (DE); Svend Matthiesen, Leverkusen (DE)

(73) Assignee: Symrise GmbH & Co. KG (DE)

( * ) Notice: Subject to any disclaimer, the term of this patent is extended or adjusted under 35 U.S.C. 154(b) by 186 days.

(21) Appl. No.: 10/028,609

(22) Filed: Dec. 19, 2001

(65) Prior Publication Data
US 2003/0008788 A1 Jan. 9, 2003

(30) Foreign Application Priority Data
Dec. 27, 2000 (DE) ........................................ 100 65 443

(51) Int. Cl.$^7$ .............................. A61K 7/46; C11D 3/50; G06F 19/00
(52) U.S. Cl. ................................ 703/2; 512/1; 510/101
(58) Field of Search .................... 703/2; 512/1; 510/101

(56) References Cited

U.S. PATENT DOCUMENTS

| | | | | |
|---|---|---|---|---|
| 3,815,405 A | * | 6/1974 | Dravnieks .................. | 73/23.34 |
| 4,072,479 A | * | 2/1978 | Sinha et al. ................... | 95/136 |
| 5,500,137 A | | 3/1996 | Bacon et al. ................ | 252/8.6 |
| 5,500,154 A | | 3/1996 | Bacon et al. ................ | 252/561 |
| 5,540,853 A | | 7/1996 | Trinh et al. ................. | 510/101 |
| 5,668,094 A | | 9/1997 | Bacon et al. ............... | 510/101 |
| 5,780,404 A | | 7/1998 | Bacon et al. ................ | 510/101 |
| 5,833,999 A | | 11/1998 | Trinh et al. ................. | 424/401 |
| 5,844,124 A | * | 12/1998 | Shimokawatoko et al. | 73/23.34 |
| 5,849,310 A | | 12/1998 | Trinh et al. ................. | 424/401 |
| 6,142,398 A | | 11/2000 | Shefer et al. ............ | 241/101.6 |

FOREIGN PATENT DOCUMENTS

| | | |
|---|---|---|
| DE | 199 12 152 | 9/2000 |
| WO | 97/30688 | 8/1997 |
| WO | 97/30689 | 8/1997 |
| WO | 97/31094 | 8/1997 |
| WO | 97/31097 | 8/1997 |
| WO | 97/34987 | 9/1997 |
| WO | 97/34988 | 9/1997 |
| WO | 97/34993 | 9/1997 |

OTHER PUBLICATIONS

The Chemistry of Odorants, 199, (date unavailable) pp. 188–200, Keith D. Perring, "Volatility and Substantivity".
The Chemistry of Odorants, 199, (date unavailable) pp. 227–232, Jenny Oliver, "Electronic Odour Sensing".
The Chemistry of Odorants, 199 (date unavailable) pp. 244–251, Karen Rossiter, "The Search For New Fragrance Ingredients".
Scent and Fragrances, (date unavailable) pp. 1–5, Günther Ohloff, translated from the German Edition Riechstoffe und Geruchssinn, published by Springer–Verlag in 1990, "The Chemical Senses".
Molecular Modelling, vol. 5, (dated unavailable), p. 50, H–D. Höltje and G. Golkers, "2 Small Molecules".
J. Chem. Soc. Perkin Trans 2, (month unavailable) 1993, pp. 799–805, A Klamt et al, "COSMO: A New Approach to Dielectric Screening in Solvents with Explicit Expressions for the Screening Energy and its Gradient".
Perfumer & Flavorist, vol. 18, Jul./Aug. 1993, pp. 45–49, Peter M. Müller, Norbert Neuner–Jehle, & Franz Etzweiler, "What Makes a Fragrance Substantive?".
JAOCS, vol. 71, No. 1, Jan. 1994, pp. 31–40, Sina D. Escher and Esther Oliveros, "A Quantitative Study of Factors That Influence the Substantivity of Fragrance Chemicals on Laundered and Dried Fabrics".
OSAR, (date unavailable) Böhm, Klebe, Kubiny, Wirkstoffdesign, pp. 363–364 [Active Ingredient Design]" Quantitative Strutktur–Wirkungsbeziehungen".
Angew. Chem., 112, (month unavailable) 2000, pp. 3107–3138, Philip Kraft, Jerzy A Bajgrowicz, Caroline Denis und Georg Frater, "Allerlei Trends: die neuesten Entwicklungen in der Riechstoffchemie".
J. Phys. Chem. 99 (month unavailable) 1995, pp. 2224–2235, Andreas Klamt, "Conductor–like Screening Model for Real Solvents: A New Approach to the Quantitative Calculation of Solvation Phenomena".
J. Phys. Chem. A (month unavailable) 1998, 102, pp. 5074–5085, Andreas Klamt, Volker Jonas, Thorsten Bürger, and John C.W. Lohrenz, "Refinement and Parametrization of COSMO–RS".
Ency. of Computational Chem., (month unavailable) 1998, pp. 604–614, Andreas Klamt, "COSMO & COSMO–RS".
Fluid Phase Equilibria, 172, (month unavailable) 2000, pp. 43–72, Andreas Klamt, Frank Eckert, "COSMO–RS: a novel and efficient method for the priori prediction of thermophysical data of liquids".
Active Ingredient Design, Bohm, Klebe, Kubinyl, Wirkstoffdesign, (date unavailable), p. 370–372, "Eigenschaften und Wirkungen: Die Hansch–Analyse".
Perfumes Art Science & Technology, P. Mëller & D. Lamparsky, (date unavailable) pp. 198–206, "The Measuring of Odors".
Perfumes Art Science & Technology, (date unavailable) pp. 172–180 "The Measuring of Odors".
Database Kosmet Online!stn: Hostynek J J (Euroerican Teachnology Resources, Inc., Lafayette, CA 94549, USA): "Predicting Absorption of Fragrance Chemical Thrjough Human Skin" retrieved from STN Database accession No. 12990 XP002197146 abstract & J Soc Cosmet Chem 1995, 46 (4) 221–229, 12 Refs.

* cited by examiner

*Primary Examiner*—John Hardee
(74) *Attorney, Agent, or Firm*—Pendorf & Cutliff

(57) ABSTRACT

A mathematical determination model is used to select odorants for products to be perfumed and for the preparation.

41 Claims, No Drawings

SELECTION METHOD FOR ODORANTS

FIELD OF THE INVENTION

The invention relates to a selection method for odorants for use in perfumed products, in which mathematical determination models are used. The invention also relates to products perfumed with odorants in which the odorants are selected using the mathematical determination models and also to a selection method for the preparation of novel odorants in which mathematical determination models are used. The invention further relates to odorants for which mathematical determination models are used for selection for the preparation of odorants as well as to products perfumed with odorants in which mathematical determination models are used for the selection for the preparation of the odorants.

BACKGROUND OF THE INVENTION

Odorants are used to improve the hedonic odor in a large number of products (perfumed consumer products). As a result of the perfuming, the impression of freshness and purity in the case of, for example, air fresheners, detergents and cleaners, and also the impression of the care action of bodycare compositions can be significantly enhanced. The use of odorants, therefore, represents a product improvement.

Throughout all of the application steps of the various perfumed consumer products, i.e. before, during and after application, some of the odorants are lost and cannot be perceived by smell by the user. Thus, for example, the formulations of various perfumed consumer products may include parts of the perfuming in such a way that the odor above the consumer product is significantly reduced. Furthermore, during the washing of laundry, for example, some of the perfuming is dissolved in the wash water and can likewise no longer be perceived by smell (U.S. Pat. No. 5,780,404).

To solve this problem, perfumers have hitherto selected, based on their experience and following laborious odor tests during washing experiments, the odorants which have a high scent intensity during and after the washing operation in the product to be perfumed in each case. In the case of these odorants, loss during the washing operation is reduced, i.e. the substantivity increases. This process is very laborious and is unable to give a comprehensive overview with regard to the suitability of all relevant odorants in all application steps of the product.

Further selection methods for odorants are described in U.S. Pat. Nos. 5,849,310, 5,833,999, 5,780,404, 5,668,094, 5,540,853, 5,500,154, 5,500,137, PCT 9,734,993, PCT 9,734,988, PCT 9,734,987, PCT 9,731,097, PCT 9,731,094, PCT 9,730,689 and PCT 9,730,688. Here, the physical parameters of the boiling point and the base-ten logarithm of the octanol/water partition coefficient (logP or $logK_{ow}$) are used as descriptors.

U.S. Pat. No. 5,780,404 describes a method of reducing the loss of odorants during the washing operation. According to this, an odorant should have a logP value above 3 and a high boiling point above 250° C. in order to be transferred as so-called enduring perfume ingredient during the washing operation onto the laundry.

This selection method is often unsatisfactory (D. Pybus, C. Sell, The Chemistry of Odorants, p. 199), since not all of the properties of the odorants and interactions with the perfumed product (perfumed phase) or the substrate to be perfumed (phase to be perfumed) are taken into consideration. In general, the logP value, being a one-dimensional representative of the polarity, has proven unsuitable for describing the molecular interactions of complex systems (H.-D. Höltje, G. Folkers, Molecular Modeling, p. 50).

For example, some of the odorants deposited onto the perfumed product, such as, for example, laundry, cannot subsequently be released into the headspace (substrate to be perfumed), but are only removed during the next washing operation. This means that some of the odorants are likewise lost or un-utilized. Consequently, what is useful is not the unlimited adhesion of an odorant, but the targeted release of the desired amount of odorants at the desired time point.

Perring (D. Pybus, C. Sell, The Chemistry of Odorants, p. 188–200) and P. Müller (P. Müller, N. Neuner-Jehle, F. Etzweiler, Perfumer & Flavorist, 1993, 18, p. 45–49) discuss the volatility and substantivity and also the quantitative structure activity relationship (QSAR) for the correlation of the experimental values against physical parameters of odorants, such as the octanol/water partition coefficient ($logK_{ow}$), the solubility in water and the vapor pressure. These physical parameters can either be determined experimentally or calculated using so-called fragment programs (clog P, Daylight, USA; Epiwin, Syracuse, USA).

For the correlation in the case of odorants, only a moderate correlation e.g. of the so-called affinity towards the $logK_{ow}$ value is described (S. Escher, E. Oliveros, JAOCS, 71, 1994, p. 31–40). On the basis of these experimental measurements and the correlations, it is not possible to adequately predict the partition behavior of odorants. In particular, the prediction of the relative headspace concentrations and the partition parameters of odorants between the perfumed phase and the phase to be perfumed has not been possible to an adequate degree.

This method permits only a rough estimation with regard to the partition behavior of odorants. However, an exact quantitative a priori prediction of odorant concentrations or partition parameters is not possible (D. Pybus, C. Sell, The Chemistry of Odorants, p. 200; P. Müller, D. Lamparsky, Perfumes, Art, Science & Technology, p. 198).

As is known, humans perceive an odor (G. Ohloff, Riechstoffe und Geruchssinn [Odorants and Sense of Smell], p. 1–5) as a result of the contact of volatile organic compounds with the olfactory mucosa present in the nose. This means that a perfume containing odorants must exist with a sufficient concentration in the headspace above the perfumed product and must not remain permanently within the perfumed consumer product or on the substrate to be perfumed. In this connection, a partition parameter is defined as the distribution of the odorant between the solid or liquid phase in the consumer product or its application form, such as, for example, an aqueous solution, on the one hand, and the gas phase surrounding the consumer product on the other hand: the higher the concentration of the odorant in the gas phase relative to the concentration of the odorant in the solid or liquid phase of the consumer product, the higher the numerical value of the partition parameter. This distribution depends individually on the formulation of the consumer product and the application step in question, and on the specific molecular properties of the odorants.

To determine the olfactory quality and suitability of odorants both from consumer products and also during and after use of the consumer products, a large number of laborious and time-consuming experimental work is usually carried out. This ascertains the odorants suitable for the perfuming. This work includes both analytical and also sensory measurements. This information is then used in the preparation of perfume oils.

It is also known that different consumer products influence the release of odorants to markedly varying degrees (P. Müller, D. Lamparsky, Perfumes, Art, Science & Technology, p. 198–206). It is noteworthy that even different formulations of a consumer product category, e.g. different washing powders, shampoo or soap formulations, differ in their odorant release behavior such that determination of the partition parameters should expediently be carried out for each individual formulation. In practice, this work cannot be carried out due to the enormous cost. Perfumes, Art, Science & Technology, p. 172–180 describes the experimental work for determining odorants in the headspace.

In a QSAR (Böhm, Klebe, Kubinyi, Wirkstoffdesign [Active Ingredient Design], p. 363), a correlation between experimental values, such as, for example, the active concentration of active ingredients, on the one hand and physicochemical values on the other hand is carried out. These physicochemical values, so-called descriptors, describe the chemical structure of the active ingredient. Within the odorant industry sector, the QSAR approach is used for explaining olfactory properties and for developing novel odorants (Angew. Chem. 2000, 112, 3106–3138; D. Pybus, C. Sell, The Chemistry of Odorants, p. 244–251).

In the field of material research, dielectric continuum models, such as, for example, COSMO (conductor-like screening model), PCM (polarizable continuum model) and AMSOL are used as mathematical methods. In addition, COSMO-RS (conductor-like screening model for real solvents) is also used as a combination of COSMO with statistical thermodynamics. The semi-empirical determination model for the method according to the present invention has been publicized (J. Chem. Soc. Perkin Trans. 2 (1993) 799, J. Phys. Chem. 99 (1995), 2224, J. Phys. Chem. 102 (1998) 5074 and "COSMO and COSMO-RS" in "Encyclopedia of Computational Chemistry" Wiley Verlag New York (1998) and Fluid Phase Equilibria 172 (2000) 43).

The calculation method has been developed for calculating partition coefficients of organic molecules in ideal and real solvents, which are present in a static partition equilibrium.

COSMO-RS has hitherto been used for calculating physicochemical constants such as the boiling point, the vapor pressure or the partition equilibrium for octanol/water ($logK_{ow}$), hexane/water, benzene/water and diethyl ether/water (J. Phys. Chem. 102 (1998) 5074) and for calculating general liquid-liquid and liquid-vapor equilibria in process engineering.

Because the service life of consumer products and of the perfuming present therein is continually becoming shorter, an ever more rapid new development of perfumings is necessary. The need for detailed investigations relating to the partition parameters of odorants, thus increases, as a function of the formulations of consumer products. Because of the large and still growing number of these investigations, it has, for years, been useful and desirable to develop a process for shortening these investigations. For this purpose, effective and reliable methods are necessary for predicting partition parameters of the odorants between different phases. These methods should permit the preparation of perfume oils, which ensure optimized release of the individual odorants at the desired point in time of application of the perfumed consumer product.

SUMMARY OF THE INVENTION

We have found a method of selecting an odorant or two or more odorants for a perfumed product, comprising the following steps in sequence:

(a) for one group of odorants, determining a parameter from the relative concentration of an odorant in the phase to be perfumed relative to the concentration in the perfumed phase, (b) determining the descriptors of odorants using a mathematical method, (c) imputting the parameters determined in step (a) into a determination model and a regression calculation is carried out, (d) calculating a prediction for all calculated odorants based on the regression calculation, (e) using the odorants most effective according to the prediction in the composition of a perfume oil.

DETAILED DESCRIPTION OF THE INVENTION

According to the method of the present invention, odorants are selected with a desired distribution between the perfumed phase and the phase to be perfumed. Thus, for example, the optimum release of odorants from the perfumed consumer product or from a perfumed substrate into the headspace to be perfumed. This produces an optimum scent impression during and after use of the consumer product. Furthermore, a more intensive and longer-lasting scent impression arises, which can be perceived by smell by the consumer.

At the same time, it is possible to minimize the amount of perfuming as a function of the scent strength to be achieved.

Surprisingly, using the mathematical determination models and the method according to the present invention, it is possible to calculate the relative headspace concentrations and the partition parameters of odorants between a perfumed phase and a phase to be perfumed in dynamic and no longer only static systems comprising complex and nonuniformly structured phases, such as, for example, consumer products, and to predict them with outstanding accuracy. This means that although consumer products often contain, for example, two or more nonideal phases and emulsions and although the determination models have been developed for calculating the static partition behavior of organic substances between two uniform solvents, it is surprisingly possible to make very good predictions for the partition behavior of odorants in consumer products.

For the purposes of the present invention, perfumed phases are gaseous, liquid, solid and semisolid perfumed products which are to attain a pleasant odor as a result of the addition of perfume oils or odorant mixtures, or in which an unpleasant odor is to be masked. The odorants are transferred from these perfumed phases into the phase to be perfumed.

Furthermore, for the purposes of the present invention, perfumed products are in principle to be understood as meaning all natural or synthetic products which are changed as a result of the addition of odorants (perfuming). The products to be perfumed can be liquid or solid, but also semisolid (e.g. wax- or gel-like).

Preferred perfumed products are, for example, use-specific consumer products for use as detergents, care compositions, air fresheners and cleaners for industrial application, in the domestic sector, for veterinary application and in body hygiene, and all application forms of the consumer products, such as, for example, aqueous solutions.

Preferred perfumed products are, for example, alcoholic fine perfumes, washing powders, fabric softener compositions, fabric softener sheets, surface cleaners, toilet cleaners, rinses, all-purpose cleaners, disinfectants, polishes, glass cleaners, dishwashing compositions, air fresheners, shampoos, conditioners, hair colorants, deodorants, antiperspirants, solid and liquid soaps, body lotions, skin creams and waxes.

For the purposes of the present invention, phases to be perfumed are gaseous, liquid, solid and semisolid substrates which are to attain a pleasant odor as a result of the transfer of the perfuming from the perfumed phase, or in which an unpleasant odor is to be masked.

Preferred substrates which are of importance for everyday use by people are the headspace to be perfumed, liquid phases to be perfumed, such as, for example, aqueous solutions, and also solid surfaces to be perfumed, such as, for example, textiles, skin, hair, plastics, metals, glass, ceramic, wood and stone.

Examples of odorants, which can be added to the products to be perfumed are given, for example, in S. Arctander, Perfume and Flavor Materials, Vol. I and II Montclair, N.J., 1969, published privately or K. Bauer, D. Garbe and H. Surburg, Common Odorant and Flavor Materials, 3rd Ed., Wiley-VCH, Weinheim 1997.

Individual examples, which may be mentioned are:

extracts from natural raw materials such as essential oils, concretes, absolutes, resins, resinoids, balsams, tinctures, such as, for example, ambergris tincture; amyris oil; angelica seed oil; angelica root oil; aniseed oil; valerian oil; basil oil; wood moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill herb oil; dill seed oil; eau de brouts absolute; oakmoss absolute; elemi oil; estragon oil; eucalyptus citriodora oil; eucalyptus oil; fennel oil; fir-needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; litsea cubeba oil; laurel oil; mace oil; marjoram oil; mandarin oil; massoi bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange-flower absolute; orange oil; origanum oil; palmarosa oil; patchouli oil; perilla oil; Peruvian balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmation sage oil; Spanish sage oil; sandalwood oil; celery seed oil; spike lavender oil; Japanese anise oil; styrax oil; tagetes oil; fir needle oil; tea-tree oil; turpentine oil; thyme oil; Tolu balsam; tonka absolute; tuberose absolute; vanilla extract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil; and fractions thereof, or ingredients isolated therefrom;

individual odorants from the group of hydrocarbons, such as, for example, 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene;

of aliphatic alcohols, such as, for example, hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; of aliphatic aldehydes and 1,4-dioxacycloalken-2-ones thereof, such as, for example, hexanal; heptanal; octanal; nonanal; decanal; undecanal; dodecanal; tridecanal; 2-methyl-octanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde;

of aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; of aliphatic sulfur-containing compounds, such as, for example, 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of aliphatic nitriles, such as, for example, 2-nonenenitrile; 2-tridecenenitrile; 2,12-tridecadienenitrile; 3,7-dimethyl-2,6-octadienenitrile; 3,7-dimethyl-6-octenenitrile;

of aliphatic carboxylic acids and esters thereof, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl 2-isoamyloxyacetate; methyl 3,7-dimethyl-2,6-octadienoate;

of acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof;

of acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

of cyclic terpene alcohols, such as, for example, menthol; isopulegol; alpha-terpineol; terpineol-4; menthan-8-ol;

menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates, 3-methyl-2-butenoates thereof;

of cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedarwood oil (methyl cedryl ketone);

of cyclic alcohols, such as, for example, 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of cycloaliphatic alcohols, such as, for example, alpha-3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of cyclic and cycloaliphatic ethers, such as, for example, cineol; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methyl propyl)-1,3-dioxane;

of cyclic ketones, such as, for example, 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone;

of cycloaliphatic aldehydes, such as, for example, 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl 2,4-dimethyl-3-cyclohexen-1-yl ketone;

of esters of cyclic alcohols, such as, for example, 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

of esters of cycloaliphatic carboxylic acids, such as, for example, allyl 3-cyclohexyl-propionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-d ioxolan-2-acetate;

of aromatic hydrocarbons, such as, for example, styrene and diphenylmethane;

of araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

of esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; of araliphatic ethers, such as, for example, 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

of aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxy-benzaldehyde; 2-methyl-3-(4-methoxyphenyl)propanal; 2-methyl-3-(4-methylenedioxyphenyl)propanal;

of aromatic and araliphatic ketones, such as, for example, acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6- tetramethyl-3-(1-methylethyl)-1H-5-indenyl]ethanone; 5',6',7',8'-tetrahydro-3',5',5',6',8',8'-hexamethyl-2-acetonaphthone;

of aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

of nitrogen-containing aromatic compounds, such as, for example, 2,4,6-trinitro-1,3-dimethyl-5-tert-butylbenzene; 3,5-dinitro-2,6-dimethyl-4-tert-butylacetophenone; cinnamonitrile; 5-phenyl-3-methyl-2-pentenenitrile; 5-phenyl-3-methylpentanenitrile; methyl anthranilate; methyl N-methylanthranilate; Schiff bases of methyl anthranilate with 7-hydroxy-3,7-dimethyloctanal; 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine;

of phenols, phenyl ethers and phenyl esters, such as, for example, estragole; anethole; eugenole; eugenyl methyl ether; isoeugenole; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

of heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

In the method according to the present invention, in a first step, a parameter (partition equilibrium) is determined as a quotient from the relative concentration of the odorant in the phase to be perfumed and the perfumed phase. Both the phase to be perfumed and the perfumed phase may be gaseous, liquid, solid or semisolid. Preferably, the phase to be perfumed is the headspace, a liquid phase above the perfumed phase or a solid substrate.

It is preferred to determine the partition equilibrium between a liquid and a solid phase.

Alternatively, it is preferred to determine the partition equilibrium between a gas phase and a solid phase.

Furthermore, it is alternatively preferred to determine the partition equilibrium between a gas phase and a liquid phase.

This distribution depends individually on the formulation of the consumer product and the respective application step and also on the specific molecular properties of the odorants. This product-specific parameter is the consequence of the specific interactions of the product or ingredients thereof with the individual odorants.

To determine the parameter, both the perfumed product, including all components such as the product to be perfumed itself, all odorants and all auxiliaries, and also simplified model products are taken into consideration.

Depending on the type of product, measurements of the odorants are made in the headspace above the perfumed product, in the individual application stages of the perfumed product e.g. measurements in and above solutions, and on and above various perfumed substrates. For example, for a handwashing soap, the relative concentration of the odorant is measured analytically above and in the soap itself, above and in a suitable aqueous solution, above and on the moist washed skin and above and on the dried skin.

For carrying out a regression calculation in the third step of the method according to the present invention, it is advantageous if 2 to 200 odorants are present as a group in the product to be investigated. It is preferred if approximately 10 to 100, and more preferred, if 20 to 50, individual odorants are present in the perfumed product to be investigated. This group of odorants, which should be structurally different, is representative of the totality of all odorants used for the perfuming of a certain consumer product. This group of odorants is incorporated into the product in a concentration customary for the type of product.

The relative concentration of the individual odorants is determined in a manner known per se by analytical methods, such as gas chromatography (GC), high performance liquid chromatography (HPLC), infrared spectrometry (IR), nuclear magnetic resonance spectrometry (NMR), mass spectrometry (MS) and ultraviolet spectrometry (UV). Furthermore, it is also possible to use signals of so-called electronic noses (D. Pybus, C. Sell, The Chemistry of Odorants, p. 227–232). Gas chromatography has proven particularly suitable for the analysis of odorants. In gas chromatography, it is also possible to use various injection methods, such as, for example, thermodesorption, liquid injection and gas injection.

Prior to analytical measurement of odorants, various enrichment processes can be carried out, such as, for example, extraction, concentration or adsorption. Suitable extractants or liquid-liquid or liquid-solid extractions are, for example, solvents, such as, for example, carbon dioxide, ethers, ketones, hydrocarbons, alcohols, water and esters.

Furthermore, by freezing out a static or dynamic headspace above the perfumed product or substrates treated with the perfumed product, such as hair, textiles, ceramic or plastics, by means of cold traps, it is possible to achieve enrichment or concentration.

Suitable for the adsorption or extraction of odorants from a static or dynamic headspace are surface-active adsorbents, such as, for example, hair, textiles, ceramic, plastics, Tenax®, Poropax® and activated carbon. The odorants enriched on these adsorbents are then desorbed using heat (thermodesorption) or solvents and can then be analyzed.

In the second step, the descriptors of odorants are determined using a mathematical method. The descriptors describe properties such as, for example, the molecular weight, the molecular volume and the polarity.

In the first substep, conformers of the three-dimensional chemical structure of odorants to be calculated are generated using programs such as, for example, Hiphop (Molecular Simulation Inc., USA) and HyperChem (Hypercube, Fla., USA).

A field of force optimization of the structures is then carried out using calculating programs such as, for example, Discover (Insight, Molecular Simulation Inc., USA), Merck Molecular Force Field (MMFF, Merck) or Open Force Field (OFF, MSI, USA).

Subsequently, using accumulation analysis by means of cluster programs such as, for example, NMRClust (Oxford Molecular Ltd, UK), those conformers are selected from the resulting molecular structures, which have the greatest possible structural diversity. In particular, conformers with a low overall energy are preferred.

Subsequent structure optimization of the selected conformers is carried out using semiempirical calculation methods such as PM3 or AM1 (AMPAC, SemiChem or MOPAC, Fujitsu Ltd).

In a further accumulation analysis, the conformers are again selected for the further calculation.

Subsequently, a structure optimization and energy minimization is carried out using ab initio processes such as, for example, Hartree-Fock or Møller-Plesset or density functional methods (DFT) such as, for example, RI-DFT (Turbomol, Chem. Phys. Letters 162 (1989) 165) or GAUSSIAN98 (Gaussian Inc.) or DMol3 (Molecular Simulations Inc.) using the COSMO option.

A DFT/COSMO calculation gives, as a result, the total energy of the electrostatically ideally shielded molecule and the resulting shield charge density a on the surface of the molecule.

In the subsequent step, COSMO-RS (COSMOlogic, Germany) is used to consider the interactions of molecules in liquid systems and amorphous solids as contact interactions of ideally shielded molecules (Fluid Phase Equilibria 172 (2000) 43).

In COSMO-RS calculations, the surface shield charge densities σ on the surface of a molecule of a substance X which are relevant for the interactions are in this case reduced to a frequency distribution $p^X(\sigma)$, which gives the composition of the sections of surface with regard to σ and is abbreviated below to σ-profile.

Subsequently, the direct or the indirect calculation of the partition parameters can be carried out using two different methods. In the direct calculation according to the known method (Fluid Phase Equilibria 172 (2000) 43), it is necessary to know the chemical composition of both phases (of the product and of the substrate), whereas for the indirect calculation using the novel method, no information with regard to the chemical composition is necessary.

If the chemical composition of the two phases, such as, for example, in the case of candle wax and air, is known, it is possible to calculate the chemical potential of any compound in the phases directly using statistical thermodynamics. The logarithmic partition parameters then arise from the difference in the chemical potentials of the odorants in the various phases.

In the rarest cases, the chemical and physical structure of the perfumed consumer products is uniform and known to a degree such that it is possible to use the above-described method. In this case, a novel procedure is used in which the assumption is made that, as is the case for simple liquids, it is also possible to express the affinity for solvate molecules of very different polarity by a σ-potential $\mu_s(\sigma)$ for complex phases S, as are generally present in the case of consumer products to be perfumed with odorants, if said potential can no longer be calculated directly using COSMO-RS. The shape of this function moves within the scope of the bandwidth of σ-potentials of organic liquids. For the calculation according to the invention, $\mu S(\sigma)$ is, therefore, expanded as a generalized Taylor series:

$$\mu_S(\sigma) \cong \sum_{i=-2}^{m} c_S^i f_i(\sigma) \quad (1)$$

where $$f_i(\sigma) = \sigma^i \text{ for } i \geq 0 \quad (2)$$

and $$f_{-2/-1}(\sigma) = f_{acc/don}(\sigma) \cong \begin{cases} 0 & \text{if } \pm\sigma < \sigma_{hb} \\ \mp\sigma + \sigma_{hb} & \text{if } \pm\sigma > \sigma_{hb} \end{cases} \quad (3)$$

(Explanation of the symbols: $\mu_S(\sigma)$: σ-potential of the phase; i: index for counting the members of the series; m: highest order of the members of the series; $f_i(\sigma)$: base function; acc: hydrogen bridge acceptor; $c_S^i$: expansion coefficient of the Taylor series; don: hydrogen bridge donor; $\sigma_{hb}$: threshold for hydrogen bridge bonds)

In the case of applications with equations, seven base functions suffice, i.e. the two hydrogen bridge functions facc (acceptor behavior), $f_{don}$ (donor behavior) and the five polynomials $M_i^X$ of the order m=0 to m=4, in order to accommodate any σ-potentials for odorants sufficiently accurately by regression. The chemical potential of a substance X in this phase S can then be written as:

$$\mu_S^X = \int p^X(\sigma)\mu_S(\sigma)d\sigma \quad (4)$$

$$\cong \int p^X(\sigma) \sum_{i=-2}^{m} c_S^i f_i(\sigma) d\sigma \cong \sum_{i=-2}^{m} c_S^i M_i^X$$

where the σ-moments $M_i^X$ of the solvate are defined as $$M_i^X = \int p^X(\sigma) f_i(\sigma) d\sigma \quad (5)$$

Using the seven σ-moments ($f_{acc}$, $f_{don}$, $M_0^X$, $M_1^X$, $M_2^X$, $M_3^X$, $M_4^X$) and $\mu_{gas}^X$, a very generally valid principle of molecule descriptors has been found which makes it possible, according to equation (4), to determine any chemical potentials of odorants in very different matrices by linear regression. The phase S is characterized here by the coefficient $c_i^S$ in front of the moments $M_i^X$. In the case of charge-neutral substances, the first moment $M_1^X$ is missing as descriptor since it describes the overall charge and assumes the numerical value zero. In the case of equilibria, which involve the gas phase, the chemical potential $\mu_{gas}^X$ of the molecule in the gas phase is to be taken into consideration as descriptor in addition to the σ-moments. This is calculated directly by the COSMOtherm software.

In the third step of the method according to the present invention, the parameters determined in the first step and the descriptors obtained in the second step, alone or in combination with already known descriptors, are input into the function equation of the mathematical determination model, and a regression calculation is carried out.

For this purpose, the measured relative concentrations of the individual odorants in the perfumed phase and the phase to be perfumed are compared. The partition parameter obtained for each individual odorant is converted to the logarithm and used as so-called activity (Y) for a regression in a calculation table against the descriptors (X), and a regression calculation is carried out in a manner known per se (Böhm, Klebe, Kubinyi, Wirkstoffdesign [Active Ingredient Design], p. 370–372).

The above described σ-moment and $\mu_{gas}^X$ can be used, alone or in combination with already known descriptors, such as, for example, logP, both for the regression of partition parameters $P^X_{gas,S}$ for substances X between the headspace to be perfumed and the perfumed phase S, and also for the regression of partition parameters $P^X_{S,S'}$ for substances X between a perfumed phase S, e.g. an aqueous washing solution, and a phase S' to be perfumed, e.g. textiles or skin.

For the distribution of substances between the headspace to be perfumed and the perfumed phase, if the setting approaches equilibrium, the logarithmic partition parameter $P^X_{gas,S}$ is expressed as chemical potential difference in the determination model (6) below:

$$\log P^X_{gas,S} = c_{gen}(\mu_{gas}^X - \mu_S^X) + const. \qquad (6)$$

$$= c_{gen}\mu_{gas}^X + c_S^0 M_0^X + c_S^2 M_2^X + c_S^3 M_3^X +$$

$$c_S^4 M_4^X + c_S^{acc} M_{acc}^X + c_S^{don} M_{don}^X + const.$$

In the determination model (6), $\mu_{gas}^X$ is the chemical potential of the odorant in the gas phase calculated directly using COSMO-RS. The coefficients $c_S^i$ characterize the liquid or solid phase S with regard to their physical mode of interaction, while the general coefficient $c_{gen}$ and the constant "const.", link together the system of units for free energies and logarithmic partition parameters. $\mu_{gas}^X$ and the above defined moments $M_i^X$ are known from the COSMO-RS calculations.

Then, if the partition parameters for a group of 2 to 200 different odorants are known by analytical measurement, if the above described COSMO-RS calculations are available, the missing coefficients for the descriptors are uniquely determined by linear regression.

For the partition parameter $P^X_{S,S'}$, which describes the distribution between a liquid or solid phase on the one hand and between a liquid or solid phase on the other hand, the gas phase potential $\mu_{gas}^X$ is insignificant. This then gives, analogous to equation (6):

$$\log P^X_{S,S'} = c_{gen}(\mu_S^X - \mu_{S'}^X) + const. \qquad (7)$$

$$= c_{S,S'}^0 M_0^X + c_{S,S'}^2 M_2^X + c_{S,S'}^3 M_3^X +$$

$$c_{S,S'}^4 M_4^X + c_{S,S'}^{acc} M_{acc}^X + c_{S,S'}^{don} M_{don}^X + const.$$

Analogous to the partition parameter $P^X_{gas,S}$, reliable regressions with regard to the partition parameter $P^X_{S,S'}$ are established by linear regression for any odorants for which the corresponding COSMO-RS calculations have been carried out.

Various regression methods, e.g. multiple linear regression, stepwise and GFA (genetic function algorithm), are used to ascertain equations which describe the mathematical relationship between the logarithmic partition parameters of the odorants and the descriptors. These equations are validated using various statistical methods, such as, for example, the correlation coefficient, standard deviation, chance test, number of degrees of freedom, number of outliers, boot strap error, cross validation, lack of fit (according to Jerome Friedman), determination of the deviations, F statistics, and other methods.

The quality of the mathematical relationship is better the closer the numerical values for the correlation coefficients $r^2$ and the cross validation $XVr^2$ come to the value 1, or the higher the numerical value for the F statistics (F test) and the lower the numerical values for the standard deviation s, outliers and lack of fit.

For the use of predictions for partition parameters of odorants, it is generally valid that the correlation coefficient $r^2$ should be greater than 0.75 for a satisfactory correlation, greater than 0.85 for a good correlation and greater than 0.90 for a very good correlation. In order that a regression can be used for the prediction, the cross validation $XVr^2$ should be greater than 0.65 and preferably greater than 0.75 and not be more than 0.1 less than the associated correlation coefficient $r^2$.

The equation with the best correlation and best validation is used in order to calculate beforehand, the logarithmic partition parameters in the determination model for all other odorants.

As a result of the regression calculation, in the fourth step of the method according to the present invention, exact predictions for the odorants under consideration with regard to the partition parameters between the perfumed phase and the phase to be perfumed are obtained as a result of inserting into equations (6) and (7) for all odorants, as a function of the coefficients and the descriptors. The prediction of the partition coefficients of the individual odorants are made available to perfumers in data banks.

From this grading or prediction, in a fifth step, the perfumer selects individual or two or more odorants which, based on the partition parameters, are particularly suitable for a perfuming of a product. More preference is given to odorants with the highest possible partition parameter. These odorants are then used with other odorants in the creative composition. The perfuming obtained in this way is then added to the product in order to satisfy the expectations of the consumers of the product with regard to its olfactory properties.

Using the odorants selected in this way, it is possible to create a perfume oil with a particularly good scent impression in one or more application stages for a consumer product.

Prior to the present invention, the mathematical description of e.g. volatilities and partition parameters of odorants was not possible or was possible only to an entirely inadequate degree (D. Pybus, C. Sell, The Chemistry of Fragrances, p. 200; P. Müller, D. Lamparsky, Perfumes, Art, Science & Technology, p. 198).

The advantage of the method according to the present invention lies in the universal and simple applicability of the calculation method for all partition parameters of odorants in any phases. The phases can have any desired composition, which does not have to be known. The parameterization of the phases takes place via the coefficients of the descriptors in the regression equations. All descriptors are derived merely by calculation from the chemical structure of the odorants and do not require experimental work. Surprisingly, as a result of the method according to the present invention, an accurate and reliable mathematical description or explanation of the experimental partition parameters of odorants is possible. The accuracy and reliability compared with known methods and processes is, thus, considerably improved. This means that by using the novel method, in contrast to existing methods, the first reliable prediction of partition parameters for odorants is possible.

As a result, laborious experimental investigations into the partition parameters of odorants as a function of the formulation of a consumer product can be replaced by rapid, effective and reliable predictions. These predictions can be used to prepare particularly effective perfumings.

By using the mathematical method within the scope of the present invention, it is possible to carry out a reliable prediction of the relative headspace concentrations and the partition parameters of odorants in various phases before, during and following application of consumer products.

As a result, it is possible to select odorants, which have an optimal partition parameter for an existing formulation, for the preparation of perfume oils. These perfume oils have both higher scent intensity and diffusion during use of the consumer product and also after use have a higher scent intensity and longer substantivity on the substrate.

As the comparison shows (see Examples), the use of known descriptors, such as the boiling point (b.p.) and the octanol-water partition coefficient (clogP, $logK_{ow}$), for explaining the experimental data and for predicting further experimental data does not give rise to results which can be used for perfumery work, since these descriptors correlate only very poorly with the experimental values (D. Pybus, C. Sell, The Chemistry of Fragrances, p. 199). Even the use of more modern descriptors, as provided by numerous suppliers, led only to a limited quality of correlation. Moreover, these mathematical models are very questionable because of the, at times, lack of connection with regard to the content and produce unsuitable predictions for further experimental measurements. These predictions are too inaccurate and cannot be usefully used for the creative composition of perfumings.

The present invention also relates to products perfumed with odorants, which are characterized in that the odorants are selected for the perfumed products using a mathematical method. This method gives predictions with regard to the relative distribution of odorants in the phase to be perfumed relative to the perfumed phase.

The products according to the present invention perfumed with odorants are markedly superior in their use to perfumed products for which the odorants have been selected in a manner known per se.

The present invention also relates to a selection process for the preparation of novel odorants, which is characterized in that mathematical determination models are used in the selection of the odorants to be prepared in a novel manner.

The novel odorants according to the present invention are markedly superior in their use to odorants, which have been selected for the preparation in a manner known per se.

The present invention also relates to odorants, which are characterized in that the selection for the preparation of the odorants is carried out using a mathematical determination model.

The novel odorants according to the present invention are markedly superior in their use to odorants, which have been selected for the preparation in a manner known per se.

The present invention also relates to products perfumed with odorants, which are characterized in that the selection for the preparation of the odorants used for the perfumed products is carried out using a mathematical method.

The products perfumed with the odorants according to the present invention are markedly superior in their use to perfumed products for which the odorants have been selected for the preparation in a manner known per se.

The advantage of the method according to the present invention lies in the universal and simple applicability of the calculation method for all partition parameters of odorants in any phases. The phases can have any desired composition, which does not have to be known. The parameterization of these phases takes place via the coefficients of the descriptors in the regression equations. All descriptors are derived merely by calculation from the chemical structure of the odorants and do not require experimental work.

EXAMPLES

In general, the analytical measurement of the relative concentration of odorants in a perfumed product, in the headspace above the perfumed product and on the perfumed substrate are carried out, by way of example, for a group of odorants.

The odorants in the headspace can be enriched using the various methods described above, and their concentrations can be measured. The enrichment method used in each case and the analytical measurement method are matched individually to the product to be measured and to the application step in each case.

The amounts of the odorants found in the headspace are compared with the amount found in the perfumed product (shampoo, soap, washing powder, candle, gel air freshener, WC block) (relative partition parameters). These values are converted to the logarithm and entered as activity values into the regression table (Table 1). Using various methods, regression against the COSMO-RS and other descriptors (e.g. c logP and boiling point) are carried out, and the best correlation according to the validation is selected. In all of the regression equations belonging to the examples, odorants with a deviation in the regression of more than +/−0.43 log units from the experimental value are defined as outliers. The COSMO-RS regression equations obtained in this way are significantly better compared with the clogP or b.p. regression equations with regard to the quality of correlation, quality of prediction and the number of outliers. In the next step, the COSMO-RS regression equation is linked to the regression table, which contains all descriptors for all odorants. The use of the COSMO-RS regression equation on all odorants gives the prediction (Table 4, 5, 7, 9, 11, 13, 15) for the logarithmic relative partition parameters for all odorants. These values are then used for the perfumery creation. The procedure is analogous in all examples.

The following chemical structure names are abbreviated: dimethylbenzylcarbinyl acetate (DMBCA), phenylethyl alcohol (PEA).

TABLE 1

Example of a regression table

| Substance | Activity | $M_0^x$ | $M_2^x$ | $M_3^x$ | $M_4^x$ | $f_{acc}$ | $f_{don}$ | $\Delta G_{Cosmo}$ |
|---|---|---|---|---|---|---|---|---|
| alpha-Pinene | | 182.94 | 15.547 | 2.0076 | 3.7672 | 0.0036 | 0 | −9.6842 |
| Amylcinnamaldehyde, α | | 270.30 | 60.582 | 22.1066 | 50.8991 | 1.4412 | 0 | −18.6148 |
| Benzyl acetate | | 197.88 | 72.379 | 27.692 | 64.7824 | 1.7606 | 0 | −16.4831 |
| Benzyl alcohol | | 150.59 | 65.602 | 6.9788 | 87.1685 | 2.333 | 1.6507 | −13.5795 |
| Benzyl salicylate | | 259.62 | 71.418 | 1.7256 | 47.1376 | 0.2492 | 0.4879 | −18.9653 |
| beta-Pinene | | 182.17 | 20.697 | 4.8988 | 7.2647 | 0.0087 | 0 | −10.232 |
| Camphene | | 179.45 | 19.913 | 4.4876 | 6.7674 | 0.0047 | 0 | −9.9874 |
| Caryophyllene | | 243.68 | 28.201 | 7.8143 | 11.5264 | 0.0747 | 0 | −14.1671 |
| Cedrol | | 253.34 | 47.908 | 15.6906 | 67.7804 | 2.3408 | 0.9288 | −16.476 |
| Cedryl acetate | | 279.10 | 50.828 | 28.4332 | 49.6005 | 1.7361 | 0 | −18.2928 |
| Citronellol | | 231.11 | 63.522 | 20.7436 | 94.9695 | 3.0534 | 1.5743 | −14.7972 |
| Coumarin | | 172.45 | 72.970 | 28.5131 | 82.5776 | 2.6523 | 0.001 | −18.9259 |
| Diethyl phthalate | | 250.88 | 88.235 | 40.9015 | 85.8762 | 2.0929 | 0 | −21.2179 |
| Dihydromyrcenol | | 227.10 | 56.430 | 24.3864 | 77.4421 | 2.8952 | 0.8139 | −14.0568 |
| DMBCA | | 235.19 | 64.333 | 26.0883 | 54.0729 | 1.5488 | 0 | −16.8222 |
| Ethylene brassylate | | 304.37 | 87.814 | 53.3295 | 94.7374 | 2.9648 | 0 | −24.9282 |
| Eugenol | | 211.09 | 71.061 | −2.7739 | 66.1703 | 0.4371 | 1.6307 | −16.2769 |
| gamma-Terpinene | | 196.66 | 24.722 | 6.1281 | 8.5462 | 0.0003 | 0 | −10.8848 |
| Geraniol | | 224.03 | 67.407 | 18.0173 | 96.9246 | 2.8774 | 1.7682 | −14.723 |
| Herbaflorat | | 224.20 | 59.936 | 33.5482 | 59.0415 | 1.7613 | 0 | −16.8667 |
| Hexylzimtaldehyde, α | | 286.74 | 62.029 | 23.913 | 51.3968 | 1.4679 | 0 | −19.5153 |
| Hydroxycitronellal | | 236.05 | 84.431 | 42.7048 | 121.5161 | 4.2171 | 1.1583 | −18.562 |
| Ionone, alpha | | 241.87 | 61.073 | 39.4863 | 70.3229 | 2.7962 | 0 | −18.1457 |
| Ionone, beta | | 244.28 | 57.905 | 39.5098 | 70.4258 | 3.0875 | 0 | −17.9204 |
| Iraldein, alpha | | 255.33 | 59.723 | 39.1916 | 68.4779 | 2.7242 | 0.0002 | −18.4167 |
| Isoamyl salicylate | | 255.85 | 62.035 | 12.2572 | 50.2951 | 0.6037 | 0.4704 | −16.697 |
| Isobornyl acetate | | 229.61 | 48.627 | 28.0637 | 49.6246 | 1.7189 | 0 | −15.726 |
| Lilial | | 261.24 | 63.727 | 24.457 | 48.0025 | 1.1775 | 0 | −19.1351 |
| Limonene D | | 196.12 | 27.540 | 8.2705 | 11.4017 | 0.0038 | 0 | −11.0721 |
| Linalool | | 221.83 | 59.129 | 20.8859 | 73.0534 | 2.4332 | 0.8688 | −13.7079 |
| Musk, ketone | | 288.19 | 84.911 | 22.3561 | 57.4895 | 0.6485 | 0 | −22.6713 |
| Musk, xylene | | 277.43 | 73.141 | 6.7028 | 35.7804 | 0 | 0 | −20.0232 |
| Oryclon | | 246.51 | 56.372 | 34.1065 | 58.5465 | 1.9711 | 0 | −16.6605 |
| Oryclon P 2 | | 243.70 | 52.932 | 32.4378 | 56.1438 | 2.0197 | 0 | −16.3314 |
| PEA | | 213.15 | 69.314 | 25.8393 | 56.9434 | 1.4132 | 0 | −16.4073 |
| Prenyl acetate | | 185.88 | 61.027 | 32.3413 | 61.077 | 1.8481 | 0 | −13.397 |
| Styrolyl acetate | | 211.06 | 66.887 | 26.2008 | 57.3712 | 1.5349 | 0 | −16.5608 |
| Terpineol | | 202.44 | 55.166 | 23.6513 | 79.1806 | 2.8931 | 0.9208 | −14.2052 |
| Terpinyl acetate | | 240.27 | 56.937 | 30.6541 | 53.5328 | 1.6327 | 0 | −16.2886 |

Application Examples

Example 1

Hair, Headspace Above the Wet Washed Hair

Example formulations for perfumed shampoos are the following:

TABLE 2

1st Shampoo, transparent

| Ingredients | | % (w/w) |
|---|---|---|
| Plantacare PS 10 (1) | Sodium Laureth Sulfate (and) Lauryl Glycoside | 20.000 |
| Demineralized water | Water (Aqua) | 75.450 |

TABLE 2-continued

1st Shampoo, transparent

| Ingredients | | % (w/w) |
|---|---|---|
| Sodium chloride | Sodium Chloride | 1.400 |
| Phenonip (2) | Phenoxyethanol (and) Methylparaben (and) Ethylparaben (and) Propylparaben (and) Butylparaben | 0.500 |
| Citric acid, 10.0% solution | Citric Acid | 1.650 |
| Perfume oil (3) | Odorant | 1.000 |

TABLE 3

2nd Shampoo, pearly luster

| Ingredients | | % (w/w) |
|---|---|---|
| Plantacare PS 10 (1) | Sodium Laureth Sulfate (and) Lauryl Glycoside | 20.000 |
| Euperlan PK 771 (1) | Glycol Distearate (and) Sodium Laureth Sulfate (and) Cocamide MEA (and) Laureth-10 | 3.000 |
| Demineralized water | Water (Aqua) | 72.650 |
| Sodium chloride | Sodium Chloride | 1.200 |
| Phenonip (2) | Phenoxyethanol (and) Methyl- paraben (and) Ethylparaben (and) Propylparaben (and) Butylparaben | 0.500 |
| Citric acid, 10.0% solution | Citric Acid | 1.650 |
| Perfume oil (3) | Odorant | 1.000 |

Suppliers:
(1) Cognis Deutschland GmbH, D-40191 Düsseldorf, Germany
(2) Nipa Laboratories Ltd., CF 382SN South Wales, U.K.
(3) Haarmann & Reimer, D-37603 Holzminden, Germany The example reflects the scent impression, which is perceived from freshly washed hair. The shampoo is prepared as is generally customary. The mixture of 39 odorants is incorporated into the above-mentioned shampoo (1$^{st}$) in an amount of 1%. A hair tress (2.5 g) is washed in 100 ml of a 20% shampoo solution in water by immersing 5–10 times and stirring, and then rinsed in 100 ml of clear water by immersing it three times. The hair tress is carefully patted with thin cellulose. The moist hair tress is transferred to a 100 ml Erlenmeyer flask sealed with a septum and left to stand for 3 h. The headspace above the washed and rinsed hair tress is extracted over 15 min using solid phase microextraction (SPME). The SPME needle is desorbed in a GC injector, and a gas chromatogram is recorded. The amounts of odorants found in the headspace are compared with the amount found in the shampoo (relative partition parameters). The analytical results are then used mathematically as described above.

A correlation in accordance with the prior art leads to the results validated below:

Correlation with clogP as descriptor: $r^2=0.01$, F Test=3, $XVr^2=-0.16$, outliers: 29 of 38 substances.

Correlation with b.p. as descriptor: $r^2=0.66$, F Test=57, $XVr^2=0.60$, outliers: 18 of 38 substances.

Correlation with b.p. and clogP as descriptors: $r^2=0.69$, F Test=32, $XVr^2=0.62$, outliers: 23 of 38 substances.

COSMO-RS correlation: $r^2=0.87$, F Test=35, $XVr^2=0.81$, with descriptors: $M_2^x$, $M_3^x$, $M_4^x$, $f_{don}$, $\Delta G_{Cosmo}$, outliers: 5 of 38 substances.

TABLE 4

Example logarithmic partition parameters above wet hair according to COSMO-RS correlation.

| Substance | Activity | Prediction | Differences |
|---|---|---|---|
| alpha-Pinene | −0.776 | −0.504 | −0.272 |
| Amylzimtaldehyde, alpha | −2.172 | −2.213 | 0.040 |
| Benzyl acetate | −1.006 | −1.172 | 0.166 |
| Benzyl alcohol | −1.867 | −1.933 | 0.065 |
| beta-Pinene | −0.647 | −0.399 | −0.248 |
| Camphene | −0.721 | −0.359 | −0.362 |
| Caryophyllene | −1.080 | −1.385 | 0.304 |
| Cedrol | −2.475 | −2.691 | 0.215 |
| Cedryl acetate | −2.685 | −2.013 | −0.673 |
| Citronellol | −1.818 | −1.832 | 0.013 |
| Coumarin | −2.891 | −2.786 | −0.105 |
| Dihydromyrcenol | −1.056 | −1.347 | 0.291 |
| DMBCA | −1.127 | −1.269 | 0.141 |
| Eugenol | −2.257 | −2.346 | 0.089 |
| gamma-Terpinene | −0.074 | −0.403 | 0.329 |
| Geraniol | −2.043 | −1.782 | −0.261 |
| Herbaflorat | −1.580 | −1.161 | −0.419 |
| Hexylcinnamaldehyde, alpha | −2.690 | −2.341 | −0.349 |
| Hydroxycitronellal | −2.381 | −2.063 | −0.318 |
| Ionone, alpha | −1.559 | −1.641 | 0.082 |
| Ionone, beta | −1.636 | −1.716 | 0.080 |
| Iraldein, alpha | −1.627 | −1.731 | 0.104 |
| Isoamyl salicylate | −1.612 | −1.858 | 0.246 |
| Isobornyl acetate | −0.741 | −1.262 | 0.521 |
| Lilial | −2.089 | −1.923 | −0.166 |
| Limonene D | −0.183 | −0.310 | 0.127 |
| Linalool | −1.119 | −1.114 | −0.006 |
| Musk, xylene | −2.974 | −2.552 | −0.422 |
| Oryclon | −0.904 | −1.190 | 0.286 |
| Oryclon P 2 | −1.086 | −1.250 | 0.164 |
| PEA | −1.349 | −1.050 | −0.299 |
| Prenyl acetate | −0.299 | −0.107 | −0.193 |
| Styrolyl acetate | −1.029 | −1.210 | 0.182 |
| Terpineol | −1.511 | −1.518 | 0.007 |
| Terpinyl acetate | −1.135 | −1.057 | −0.078 |

From a list with these and further odorants with predicted partition parameters, the perfumer selects individual or many odorants which are particularly suitable within the scope of the method according to the present invention for a perfuming of wet hair using this shampoo. Using these odorants, hedonically outstanding perfumings are created which achieve a superior scent impression.

Example 2

Shampoo, Headspace Above the Shampoo

The example reflects the scent impression, which is perceived from a freshly opened bottle of shampoo. The mixture of 39 odorants is incorporated into the above-mentioned shampoo (1) in an amount of 1%. 20 g of the shampoo are transferred to a 100 ml Erlenmeyer flask sealed with a septum. The headspace above the shampoo is extracted using a SPME over 15 min. The amounts of odorants found in the headspace are compared with the amount present in the shampoo (relative partition parameters). The analytical results are then used mathematically as described above.

Correlation with clogP: $r^2=0.03$, F Test=0.6, $XVr^2=-0.15$, outliers: 16 of 28 substances.

Correlation with b.p.: $r^2=0.71$, F Test=55, $XVr^2=0.65$, outliers: 11 of 28 substances.

Correlation with b.p. and clogP: $r^2=0.72$, F Test=27, $XVr^2=0.63$, with descriptors: b.p., clogP, outliers: 11 of 28 substances.

COSMO-RS correlation: $r^2=0.92$, F Test=54, $XVr^2=0.86$, with descriptors: $M_2^x$, $M_3^x$, $f_{don}$, $\Delta G_{Cosmo}$, outliers: 2 of 28 substances.

TABLE 5

Example logarithmic partition parameters above shampoo according to COSMO-RS correlation

| Substance | Activity | Prediction | Differences |
| --- | --- | --- | --- |
| alpha-Pinene | 0.769 | 1.016 | −0.247 |
| Benzyl acetate | −0.293 | −0.331 | 0.039 |
| Benzyl alcohol | −0.759 | −1.198 | 0.439 |
| beta-Pinene | 0.830 | 0.932 | −0.102 |
| Camphene | 0.777 | 1.016 | −0.239 |
| Caryophyllene | −0.279 | −0.590 | 0.311 |
| Citronellol | −1.406 | −1.492 | 0.086 |
| Dihydromyrcenol | −0.287 | −0.494 | 0.208 |
| DMBCA | −0.513 | −0.683 | 0.169 |
| gamma-Terpinene | 1.009 | 0.752 | 0.256 |
| Geraniol | −1.839 | −1.613 | −0.226 |
| Herbaflorat | −1.062 | −0.686 | −0.376 |
| Ionone, alpha | −1.157 | −1.133 | −0.024 |
| Ionone, beta | −1.282 | −1.103 | −0.179 |
| Iraldein, alpha | −1.495 | −1.287 | −0.208 |
| Isoamyl salicylate | −1.716 | −1.367 | −0.349 |
| Isobornyl acetate | −0.026 | −0.517 | 0.490 |
| Lilial | −1.900 | −1.739 | −0.161 |
| Limonene D | 0.965 | 0.765 | 0.200 |
| Linalool | −0.511 | −0.390 | −0.121 |
| Oryclon | −0.384 | −0.665 | 0.281 |
| Oryclon P2 | −0.562 | −0.622 | 0.060 |
| PEA | −0.742 | −0.394 | −0.348 |
| Prenyl acetate | 0.844 | 0.847 | −0.003 |
| Styrolyl acetate | −0.232 | −0.510 | 0.278 |
| Terpineol | −1.098 | −0.707 | −0.390 |
| Terpinyl acetate | −0.561 | −0.542 | −0.019 |

From a list with these and other odorants with predicted partition parameters, the perfumer selects individual or many odorants, which are particularly suitable within the scope of the method according to the invention for a perfuming of this shampoo. Using these odorants, hedonically outstanding perfumings are created which achieve a superior scent impression.

Example 3

Soap, Headspace Above the Soap Bar

An example formulation of perfumed soap is as follows:

TABLE 6

Soap formulation

| Ingredients | | % (w/w) |
| --- | --- | --- |
| Soap base (1) | Sodium Tallowate, Sodium Cocoate | 98.300 |
| Bayertitan AZ (2) | Titanium Dioxide | 0.300 |
| Tinopal CBS-X (3) | Disodium Distyrylbiphenyl Disulfonate | 0.200 |

Suppliers:
(1) Enzian Seifenfabrik, 72555 Metzingen, Germany
(2) Bayer AG, Bayerwerk, D-51368 Leverkusen, Germany
(3) Ciba Spezialitätenchemie AG, 4000 Basel, Switzerland
(4) Haarmann & Reimer GmbH, D-37603 Holzminden, Germany The example reflects the scent impression, which is perceived from a fresh bar of soap. The mixture of 39 odorants is incorporated into the above-mentioned soap in an amount of 1.2%. 20 g of the grated soap are transferred to a 100 ml Erlenmeyer flask sealed with a septum. The headspace above the shampoo is extracted using a SPME over 15 min. The amounts of odorants found in the headspace are compared with the amount present in the soap (relative partition parameters). The analytical results are then used mathematically as described above.

Correlation with clogP: $r^2=0.05$, F Test=1.8, $XVr^2=−0.09$, outliers: 26 of 36 substances.

Correlation with b.p.: $r^2=0.71$, F Test=78, $XVr^2=0.66$, outliers: 13 of 36 substances.

Correlation with b.p. and clogP: $r^2=0.71$, F Test=39, $XVr^2=0.64$, outliers: 12 of 36 substances.

COSMO-RS correlation: $r^2=0.88$, F Test=38, $XVr^2=0.82$, with descriptors: $M_2^x$, $M_3^x$, $M_4^x$, $f_{acc}$, $\Delta G_{Cosmo}$, outliers: 6 of 36 substances.

TABLE 7

Example logarithmic partition parameters above soap according to COSMO-RS correlation

| Substance | Activity | Prediction | Differences |
| --- | --- | --- | --- |
| alpha-Pinene | 0.395 | 0.687 | −0.291 |
| Amylcinnamaldehyde, alpha | −1.700 | −1.376 | −0.323 |
| Benzyl acetate | 0.538 | 0.378 | 0.161 |
| Benzyl alcohol | −0.088 | −0.419 | 0.330 |
| beta-Pinene | 0.469 | 0.732 | −0.263 |
| Camphene | 0.392 | 0.809 | −0.417 |
| Caryophyllene | −0.150 | −0.841 | 0.691 |
| Cedrol | −2.090 | −2.151 | 0.061 |
| Cedryl acetate | −2.483 | −1.690 | −0.793 |
| Citronellol | −0.787 | −0.921 | 0.134 |
| Coumarin | −1.192 | −1.445 | 0.253 |
| Diethyl phthalate | −1.742 | −1.534 | −0.208 |
| Dihydromyrcenol | 0.076 | 0.010 | 0.066 |
| DMBCA | 0.059 | −0.057 | 0.116 |
| Eugenol | −1.435 | −1.615 | 0.180 |
| gamma-Terpinene | 0.819 | 0.714 | 0.104 |
| Geraniol | −0.952 | −0.843 | −0.109 |
| Herbaflorat | −0.526 | −0.525 | −0.001 |
| Hexylcinnamaldehyde, alpha | −2.176 | −1.690 | −0.486 |
| Hydroxycitronellal | −1.804 | −1.279 | −0.525 |
| Ionone, alpha | −0.701 | −0.930 | 0.229 |
| Ionone, beta | −0.837 | −0.895 | 0.058 |
| Iraldein, alpha | −0.935 | −1.147 | 0.212 |
| Isoamyl salicylate | −1.190 | −1.077 | −0.113 |
| Isobornyl acetate | 0.147 | −0.535 | 0.682 |
| Lilial | −1.331 | −1.287 | −0.044 |
| Limonene D | 0.748 | 0.747 | 0.001 |
| Linalool | −0.028 | 0.325 | −0.354 |
| Musk, xylene | −2.397 | −1.347 | −1.050 |
| Oryclon | −0.154 | −0.550 | 0.396 |
| Oryclon P2 | −0.266 | −0.547 | 0.280 |
| PEA | 0.170 | 0.348 | −0.178 |
| Prenyl acetate | 1.180 | 1.375 | −0.196 |
| Styrolyl acetate | 0.486 | 0.096 | 0.390 |
| Terpineol | −0.430 | −0.348 | −0.082 |
| Terpinyl acetate | −0.253 | −0.290 | 0.038 |

From a list with these and other odorants with predicted partition parameters, the perfumer selects individual or many odorants which are particularly suitable within the scope of the method according to the present invention for a perfuming of this soap mass. Using these odorants, hedonically outstanding perfumings are created which achieve a superior scent impression.

Example 4

Washing Powder—Headspace Above the Powder

An example formulation for perfumed washing powder is as follows:

TABLE 8

Washing powder

| Ingredients | | Amount |
|---|---|---|
| Marlon A (1) | Sodium laurylbenzene sulfonate, approx. 80% | 7.0% |
| Marlipal 013 (1) | C13/15-Oxoalcoholpolyglycolether | 4.0% |
| Prisavon (2) | Soybean/Coco soap, approx. 25% fatty acid | 3.5% |
| Thylose (3) | Carboxymethylcellulose | 1.5% |
| Tinopal (4) | Optical brightener | 0.2% |
| Optimase (5) | Enzymes | 0.6% |
| Water glass (6) | Sodium disilicate | 5.0% |
| Magnesium silicate (6) | Magnesium silicate | 2.0% |
| Sodium perborate (1) | Sodium perborate (tetrahydrate) | 20.0% |
| TAED (3) | Bleach activator | 3.0% |
| Sodium tripolyphosphate (1) | Sodium tripolyphosphate or Zeolithe | 26.0% |
| Perfume oil (7) | Odorant | 0.4% |
| Sodium sulfate (6) | Sodium sulfate (anhydrous) | 26.8% |

Suppliers:
(1) Degussa-Hüls AG, D-60287 Frankfurt, Germany
(2) Uniqema Chemie, NL-2800 AA Gouda, Netherlands
(3) Clariant GmbH, D-29699 Frankfurt, Germany
(4) Ciba Spezialitätenchemie AG, 4000 Basel, Switzerland
(5) Genecore Int. GmbH, D-31564 Nienburg, Germany
(6) Merck KGaA, D-64293 Darmstadt, Germany
(7) Haarmann & Reimer GmbH, D-37603 Holzminden, Germany The example reflects the scent impression, which is perceived from a freshly opened pack of laundry detergent. The mixture of 39 odorants is incorporated in the abovementioned washing powder in an amount of 0.5%. 20 g of the washing powder are transferred to a 100 ml Erlenmeyer flask sealed with a septum. The headspace above the shampoo is extracted using a SPME over 15 min. Using the measurement results of a GC analysis, the procedure is as in the first example. The amounts of odorants in the headspace are compared with the amount present in the washing powder (relative partition parameters). The analytical results are then used mathematically as described above.

Correlation with clogP: $r^2=0.02$, F Test=0.7, $XVr^2=-0.11$, with descriptors: AlogP, outliers: 26 of 37 substances.

Correlation with b.p.: $r^2=0.79$, F Test=123, $XVr^2=0.77$, with descriptors: b.p., outliers: 11 of 37 substances.

Correlation with b.p. and clogP: $r^2=0.79$, F Test=62, $XVr^2=0.76$, with descriptors: b.p., AlogP, outliers: 11 of 37 substances.

COSMO-RS correlation: $r^2=0.90$, F Test=40, $XVr^2=0.83$, with descriptors: $M_2^x$, $M_3^x$, $M_4^x$, $f_{acc}$, $f_{don}$, $\Delta G_{Cosmo}$, outliers: 4 of 37 substances.

TABLE 9

Example logarithmic partition parameters above washing powder according to COSMO-RS correlation

| Substance | Activity | Prediction | Differences |
|---|---|---|---|
| alpha-Pinene | 0.377 | 0.652 | −0.275 |
| Amylzimtaldehyde, alpha | −0.799 | −1.332 | 0.533 |
| Benzyl acetate | 0.224 | 0.052 | 0.173 |
| Benzyl alcohol | −0.389 | −0.564 | 0.175 |
| Benzyl salicylate | −2.349 | −1.904 | −0.444 |
| beta-Pinene | 0.415 | 0.666 | −0.252 |
| Camphene | 0.357 | 0.734 | −0.377 |
| Caryophyllene | −0.385 | −0.688 | 0.303 |

TABLE 9-continued

Example logarithmic partition parameters above washing powder according to COSMO-RS correlation

| Substance | Activity | Prediction | Differences |
|---|---|---|---|
| Cedrol | −1.547 | −1.865 | 0.319 |
| Cedryl acetate | −1.971 | −1.446 | −0.525 |
| Citronellol | −0.780 | −0.820 | 0.040 |
| Coumarin | −1.655 | −1.687 | 0.032 |
| Diethyl phthalate | −2.124 | −1.815 | −0.309 |
| Dihydromyrcenol | 0.184 | 0.057 | 0.127 |
| DMBCA | −0.041 | −0.165 | 0.124 |
| Eugenol | −1.440 | −1.828 | 0.388 |
| gamma-Terpinene | 0.771 | 0.660 | 0.110 |
| Geraniol | −0.976 | −0.789 | −0.188 |
| Herbaflorat | −0.717 | −0.586 | −0.131 |
| Hexylzimtaldehyde, alpha | −1.559 | −1.570 | 0.011 |
| Hydroxycitronellal | −1.609 | −1.219 | −0.389 |
| Ionone, alpha | −0.697 | −0.759 | 0.062 |
| Ionone, beta | −0.778 | −0.634 | −0.145 |
| Iraldein, alpha | −1.036 | −0.934 | −0.102 |
| Isoamyl salicylate | −1.467 | −1.287 | −0.180 |
| Isobornyl acetate | 0.061 | −0.486 | 0.547 |
| Lilial | −1.448 | −1.217 | −0.231 |
| Linalool | 0.057 | 0.279 | −0.222 |
| Musk, xylene | −2.764 | −1.522 | −1.242 |
| Oryclon | −0.246 | −0.527 | 0.281 |
| Oryclon P2 | −0.345 | −0.478 | 0.133 |
| PEA | −0.176 | 0.075 | −0.251 |
| Prenyl acetate | 1.167 | 1.018 | 0.149 |
| Styrolyl acetate | 0.246 | −0.121 | 0.368 |
| Terpineol | −0.390 | −0.273 | −0.116 |
| Terpinyl acetate | −0.196 | −0.327 | 0.131 |

From a list with these and other odorants with predicted partition parameters, the perfumer selects individual or many odorants, which are particularly suitable within the scope of the method according to the present invention for a perfuming of this washing powder. Using these odorants, hedonically outstanding perfumings are created which achieve a superior scent impression.

Example 5

Candle Wax—Headspace Above the Wax

An example formulation for a scented candle is as follows:

TABLE 10

Scented candle

| Ingredients | | % (w/w) |
|---|---|---|
| Paraffin 10808 (1) | Paraffin, solidification point around 64° C. | 60.0 |
| Stearine (1) | Stearic acid | 35.0 |

Suppliers:
(1) DEA Mineralöl AG, D-20457 Hamburg, Germany
(2) Haarmann & Reimer GmbH, D-37603 Holzminden, Germany The example reflects the scent impression, which is perceived from a nonburning candle. The mixture of 39 odorants is incorporated into a candle in an amount of 5%. 20 g of the grated candle are transferred to a 100 ml Erlenmeyer flask sealed with a septum. The headspace above the candle is extracted using a SPME over 15 min. The amounts of odorants found in the headspace are compared with the amount present in the candle wax (relative partition parameters). The analytical results are then used mathematically as described above.

Correlation with clogP: $r^2=0.01$, F Test=0.2, $XVr^2=-0.16$, outliers: 19 of 29 substances.

Correlation with b.p.: $r^2=0.82$, F Test=121, $XVr^2=0.80$, outliers: 6 of 29 substances.

Correlation with b.p. and clogP: $r^2=0.82$, F Test=58, $XVr^2=0.77$, outliers: 7 of 29 substances.

COSMO-RS correlation: $r^2=0.95$, F Test=86, $XVr^2=0.90$, with descriptors: $M_0^x$, $M_2^x$, $M_3^x$, $M_4^x$, $\Delta G_{Cosmo}$, outliers: 1 of 29 substances.

TABLE 11

Example logarithmic partition parameters above candle wax according to COSMO-RS correlation

| Substance | Activity | Prediction | Differences |
|---|---|---|---|
| alpha-Pinene | 0.819 | 0.748 | 0.071 |
| Benzyl acetate | −0.244 | −0.386 | 0.142 |
| Benzyl alcohol | −0.364 | −0.310 | −0.053 |
| beta-Pinene | 0.701 | 0.747 | −0.046 |
| Camphene | 0.783 | 0.830 | −0.047 |
| Caryophyllene | −1.062 | −0.908 | −0.154 |
| Citronellol | −1.159 | −1.124 | −0.035 |
| Coumarin | −1.794 | −1.687 | −0.107 |
| Diethyl phthalate | −2.459 | −2.084 | −0.375 |
| Dihydromyrcenol | −0.324 | −0.602 | 0.278 |
| DMBCA | −0.856 | −0.866 | 0.010 |
| Eugenol | −0.822 | −1.264 | 0.442 |
| gamma-Terpinene | 0.342 | 0.587 | −0.245 |
| Geraniol | −1.273 | −0.999 | −0.274 |
| Herbaflorat | −1.303 | −0.954 | −0.348 |
| Hydroxycitronellal | −1.869 | −1.844 | −0.025 |
| Ionone, alpha | −1.441 | −1.642 | 0.201 |
| Ionone, beta | −1.606 | −1.704 | 0.098 |
| Iraldein, alpha | −1.867 | −1.848 | −0.019 |
| Isobornyl acetate | −0.588 | −0.933 | 0.346 |
| Lilial | −2.105 | −1.908 | −0.197 |
| Linalool | −0.420 | −0.293 | −0.127 |
| Oryclon | −0.872 | −1.108 | 0.235 |
| Oryclon P2 | −1.048 | −1.099 | 0.051 |
| PEA | −0.632 | −0.430 | −0.202 |
| Prenyl acetate | 0.726 | 0.684 | 0.042 |
| Styrolyl acetate | −0.341 | −0.598 | 0.257 |
| Terpineol | −0.824 | −0.669 | −0.156 |
| Terpinyl acetate | −0.979 | −0.866 | −0.113 |

From a list with these and other odorants with predicted partition parameters, the perfumer selects individual or many odorants, which are particularly suitable within the scope of the method according to the present invention for a perfuming of the candle wax. Using these odorants, hedonically outstanding perfumings are created which achieve a superior scent impression.

Example 6

Gel Room Air Freshener—Headspace Above the Fresh Gel

An example formulation for a gel room air freshener is as follows:

TABLE 12

Gel room air freshener

| Ingredients | | % (w/w) |
|---|---|---|
| Demineralized water | | 89.4 |
| Genugel X-6424 (1) | Carrageenan | 2.0 |
| Arkopal N 100 (3) or Tergitol NP 10 (4) | Emulsifier | 3.5 |
| Preventol D 7 (5) | Preservative | 5.0 |

Suppliers:
(1) Hercules via: Pomosin GmbH, D-63065 Offenbach, Germany
(2) Haarmann & Reimer GmbH, 37603 Holzminden, Germany
(3) Clariant GmbH, D-60596 Frankfurt, Germany
(4) Union Carbide GmbH, D-40470 Düsseldorf, Germany
(5) Bayer AG, D-51368 Leverkusen, Germany The example reflects the scent impression, which is perceived above a fresh gel room air freshener. The mixture of 39 odorants is incorporated into an air freshener in an amount of 5%. 100 g of the air freshener are placed in its customary presentation form in a large sealed 10 liter vessel. The air freshener is left to stand for one hour. The headspace above the air freshener is extracted using a SPME over 15 min. The amounts of the odorants found in the headspace are compared with the amount present in the gel room air freshener (relative partition parameters). The analytical results are then used mathematically as described above.

Correlation with clogP: $r^20.04$, F Test=1.2, $XVr^2=-0.13$, outliers: 29 of 37.

Correlation with b.p.: $r^2=0.55$, F Test=34, $XVr^2=0.47$, outliers: 23 of 37.

Correlation with b.p. and clogP: $r^2=0.55$, F Test=17, $XVr^2=0.43$, outliers: 22 of 37.

COSMO-RS correlation: $r^2=0.75$, F Test=11, $XVr^2=0.59$, with descriptors: $M_0^x$, $M_2^x$, $M_3^x$, $M_4^x$, $f_{acc}$, $f_{don}$, $\Delta G_{Cosmo}$, outliers: 12 of 37.

TABLE 13

Example logarithmic partition parameters above gel room air fresheners according to COSMO-RS correlation

| Substance | Activity | Prediction | Differences |
|---|---|---|---|
| alpha-Pinene | −0.273 | −0.039 | −0.234 |
| Amylzimtaldehyde, alpha | −2.358 | −1.976 | −0.382 |
| Benzyl acetate | 0.594 | 0.384 | 0.210 |
| Benzyl alcohol | 0.148 | 0.433 | −0.286 |
| beta-Pinene | −0.090 | 0.247 | −0.337 |
| Camphene | −0.116 | 0.310 | −0.426 |
| Caryophyllene | −0.011 | −0.884 | 0.873 |
| Cedrol | −1.761 | −1.720 | −0.041 |
| Cedryl acetate | −2.566 | −1.332 | −1.234 |
| Citronellol | −0.158 | −0.463 | 0.305 |
| Coumarin | −2.228 | −2.465 | 0.237 |
| Diethyl phthalate | −2.303 | −1.885 | −0.418 |
| Dihydromyrcenol | 0.460 | −0.079 | 0.539 |
| DMBCA | 0.125 | 0.114 | 0.011 |
| Eugenol | −0.653 | −1.093 | 0.440 |
| gamma-Terpinene | 0.126 | 0.307 | −0.181 |
| Geraniol | −0.365 | −0.089 | −0.276 |
| Herbaflorat | −0.441 | 0.117 | −0.558 |
| Hydroxycitronellal | −1.161 | −0.786 | −0.376 |
| Ionone, alpha | −0.515 | −0.715 | 0.200 |
| Ionone, beta | −0.662 | −0.636 | −0.026 |
| Iraldein, alpha | −1.063 | −0.978 | −0.085 |
| Isoamyl salicylate | −1.544 | −1.514 | −0.031 |
| Isobornyl acetate | 0.392 | −0.592 | 0.985 |
| Lilial | −1.548 | −1.354 | −0.194 |
| Limonene D | 0.062 | 0.423 | −0.362 |
| Linalool | 0.376 | 0.450 | −0.074 |
| Oryclon | 0.089 | −0.450 | 0.540 |
| Oryclon P2 | −0.096 | −0.520 | 0.425 |
| PEA | 0.245 | 0.523 | −0.278 |

TABLE 13-continued

Example logarithmic partition parameters above gel room air fresheners according to COSMO-RS correlation

| Substance | Activity | Prediction | Differences |
|---|---|---|---|
| Prenyl acetate | 0.674 | 0.971 | −0.298 |
| Styrolyl acetate | 0.568 | 0.124 | 0.444 |
| Terpineol | 0.200 | 0.335 | −0.135 |
| Terpinyl acetate | −0.029 | −0.133 | 0.105 |

From a list with these and other odorants with predicted partition parameters, the perfumer selects individual or many odorants which are particularly suitable within the scope of the method according to the present invention for a perfuming of this gel room air freshener. Using these odorants, hedonically outstanding perfumings are created which achieve a superior scent impression.

Example 7

WC Scented Block Cleaner—Headspace Above the Solution

An example formulation of perfumed WC scented block cleaners is as follows:

TABLE 14

WC scented block cleaner

| Ingredients | | % (w/w) |
|---|---|---|
| Marlipal 1618/25 (1) | Fatty alcohol polyglycol ether, 25 EO | 65.0 |
| Lipoxol 6000 (1) | Polyethylene glycol | 14.0 |
| Maripal 013/120 (1) | Oxo alcohol polyglycol ether, 12 EO | 5.0 |
| Comperlan 100 (2) | Coconut fatty acid monoethanolamide | 5.0 |
| KLE-Wax (3) | Ester wax containing emulsifier | 5.0 |

Suppliers:
(1) Condea Chemie GmbH, D-45764 Marl, Germany
(2) Cognis GmbH, D-40551 Düsseldorf, Germany
(3) Clariant GmbH, D-60596 Frankfurt, Germany
(4) Haarmann & Reimer GmbH, D-37603 Holzminden, Germany The example reflects the scent impression, which is perceived from a WC scented block cleaner. The mixture of 39 odorants is incorporated into the toilet block in an amount of 1%. A 1% solution of the toilet block in water is prepared. 20 ml of this solution are transferred to a 100 ml Erlenmeyer flask sealed with a septum. The headspace above the shampoo is extracted by means of a SPME over 15 min. The amounts of the odorants found in the headspace are compared with the amount present in the WC block (relative partition parameters). The analytical results are then used mathematically as described above.

Correlation with clogP: $r^2=0.14$, F Test=5, $XVr^2=0.02$, outliers: 14 of 36.

Correlation with b.p.: $r^2=0.07$, F Test=2, $XVr^2=-0.12$, outliers: 15 of 36.

Correlation with b.p. and clogP: $r^2=0.26$, F Test=6, $XVr^2=0.04$, outliers: 15 of 36.

COSMO-RS correlation: $r^2=0.81$, F Test=18, $XVr^2=0.67$, with descriptors: $M_0^x$, $M_2^x$, $M_3^x$, $M_4^x$, $f_{acc}$, $\Delta G_{Cosmo}$, outliers: 5 of 36.

TABLE 15

Example logarithmic partition parameters above dissolved WC scented block cleaners according to COSMO-RS correlation

| Substance | Activity | Prediction | Differences |
|---|---|---|---|
| alpha-Pinene | −1.833 | −1.459 | −0.373 |
| Amylzimtaldehyde, alpha | −1.336 | −1.379 | 0.043 |
| Benzyl acetate | −1.552 | −1.807 | 0.255 |
| Benzyl salicylate | −3.166 | −2.659 | −0.507 |
| beta-Pinene | −1.682 | −1.352 | −0.330 |
| Camphene | −1.348 | −1.373 | 0.025 |
| Caryophyllene | −0.390 | −1.065 | 0.675 |
| Cedrol | −1.348 | −1.675 | 0.327 |
| Cedryl acetate | −1.161 | −0.603 | −0.558 |
| Citronellol | −1.575 | −1.465 | −0.110 |
| Coumarin | −3.003 | −2.961 | −0.042 |
| Dihydromyrcenol | −1.131 | −1.383 | 0.251 |
| DMBCA | −0.992 | −1.339 | 0.348 |
| Eugenol | −2.412 | −2.631 | 0.219 |
| gamma-Terpinene | −1.230 | −1.226 | −0.004 |
| Geraniol | −2.045 | −1.662 | −0.383 |
| Herbaflorat | −1.259 | −0.652 | −0.607 |
| Hexylzimtaldehyde, alpha | −1.413 | −1.192 | −0.222 |
| Ionone, alpha | −1.152 | −0.916 | −0.237 |
| Ionone, beta | −0.819 | −1.078 | 0.259 |
| Iraldein, alpha | −0.959 | −0.721 | −0.238 |
| Isoamyl salicylate | −0.870 | −1.159 | 0.289 |
| Isobornyl acetate | −0.434 | −0.801 | 0.367 |
| Lilial | −1.400 | −1.325 | −0.075 |
| Limonene D | −1.102 | −1.046 | −0.056 |
| Linalool | −1.299 | −1.453 | 0.154 |
| Oryclon | −0.390 | −0.351 | −0.039 |
| Oryclon P2 | −0.446 | −0.531 | 0.085 |
| PEA | −1.636 | −1.522 | −0.114 |
| Prenyl acetate | −1.070 | −0.748 | −0.322 |
| Styrolyl acetate | −1.320 | −1.590 | 0.270 |
| Terpineol | −1.762 | −1.739 | −0.023 |
| Terpinyl acetate | −0.524 | −0.533 | 0.009 |

From a list with these and further odorants with predicted partition parameters, the perfumer selects individual or many odorants which are particularly suitable within the scope of the method according to the present invention for a perfuming of this solution of the WC scented block cleaner. Using these odorants, hedonically outstanding perfumings are created with achieve a superior scent impression.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of selecting an odorant or two or more odorants for a perfumed product, comprising the following steps in sequence:
    (a) for one group of odorants, determining a parameter from the relative concentration of an odorant in the phase to be perfumed relative to the concentration in the perfumed phase;
    (b) determining the descriptors of odorants using a mathematical method;
    (c) imputing the parameters determined in step (a) into a determination model and carrying out a regression calculation;
    (d) calculating a prediction for all calculated odorants based on the regression calculation; and
    (e) using the odorants most effective according to the prediction in the composition of a perfume oil.

2. A method according to claim 1, wherein the determination of the relative distribution of odorants is carried out by analysis of the concentration in the perfumed phase and the phase to be perfumed.

3. A method according to claim 1, wherein the partition equilibrium between the gas phase and a liquid phase is determined.

4. A method according to claim 1, wherein the partition equilibrium between the gas phase and a solid phase is determined.

5. A method according to claim 1, wherein the partition equilibrium between a liquid phase and a solid phase is determined.

6. A method according to claim 1, wherein the partition equilibrium between two liquid phases is determined.

7. A method according to claim 1, wherein the group of odorants comprises 2 to 200 individual compounds.

8. A method according to claim 7, wherein the group of odorants comprises 10 to 100 individual compounds.

9. A method according to claim 8, wherein the group of odorants comprises 20 to 50 individual compounds.

10. A method according to claim 1, wherein, during the calculation of the descriptors, of the odorants using a mathematical method, the following steps in sequence are performed:
    (a) generating conformers;
    (b) optimizing the field of force;
    (c) selecting the conformers by accumulation analysis;
    (d) performing a semi-empirical structure optimization;
    (e) selecting further conformers by accumulation analysis;
    (f) optimizing the structure using ab-initio or DFT calculations; and
    (g) carrying out a COSMO-RS calculation.

11. A method according to claim 1, wherein a dielectric continuum calculating method is used to calculated descriptors of the odorants.

12. A method according to claim 1, wherein a mathematical determination model for the distribution between: (a) the gas phase and (b) a liquid or solid phase is described by the function $$\log P^X_{gas,S} = C_{gen}(\mu^X_{gas} - \mu^X_S) + const.$$
$$= C_{gen}\mu^X_{gas} + C^0_S M^X_0 + C^2_S M^X_2 + C^3_S M^X_3 +$$
$$C^4_S M^X_4 + C^{acc}_S M^X_{acc} + C^{don}_S M^X_{don} + const.$$

in which the symbols have the following meanings:
  $p^X_{gas,S}$ represents a partition parameter between gas phase and liquid or solid phase;
  $C_{gen}$ represents a general, customized preliminary factor;
  $\mu^X_{gas}$ represents the chemical potential of substance X in the gas phase according to COSMO-RS;
  $\mu^X_S$ represents the chemical potential of substance X in the solid or liquid phase from regression;
  const. represents the general regression constant;
  $c^i_S$ represents the expansion coefficient of the Taylor series from regression;
  acc represents the hydrogen bridge acceptor;
  don represents the hydrogen bridge donor; and
  $M^X_i$ represents the σ-moment of the i-th order of the substance X.

13. A method according to claim 1, wherein a mathematical determination model for the distribution between: (a) a liquid or solid phase and (b) a liquid or solid phase is described by the function $$\log P^X_{S,S'} = c_{gen}(\mu^X_S - \mu^X_{S'}) + const.$$
$$= c^0_{S,S'} M^X_0 + c^2_{S,S'} M^X_2 + c^3_{S,S'} M^X_3 +$$
$$c^4_{S,S'} M^X_4 + c^{acc}_{S,S'} M^X_{acc} + c^{don}_{S,S'} M^X_{don} + const.$$

in which the symbols have the following meanings:
  $p^X_{s,s'}$ represents the partition parameter between liquid phase S and liquid or solid phase S';
  $c_{gen}$ represents the general, customized preliminary factor;
  $\mu^X_s$ represents the chemical potential of substance X in the liquid phase S according to COSMO-RS;
  $\mu^X_{s'}$ represents the chemical potential of substance X in the solid or liquid phase S' from regression;
  const represents the general regression constant;
  $c^i_S$ represents the expansion coefficient of the Taylor series from regression;
  acc represents the hydrogen bridge acceptor;
  don represents the hydrogen bridge donor; and
  $M^X_i$ represents the σ-moment of the i-th order of the substance X.

14. A method according to claim 12, wherein a mathematical determination model is created using the σ-moments $M^X_0$, $M^X_2$, $M^X_2$, $M^X_4$, and $M^X_{acc}$, $M^X_{don}$ and $\mu^X_{gas}$ as descriptors and a constant.

15. A method according to claim 12, wherein a mathematical determination model is created using the σ-moments $M^X_0$, $M^X_2$, $M^X_2$, $M^X_4$, and $M^X_{acc}$, $M^X_{don}$ and $\mu^X_{gas}$ as descriptors and a constant in combination with descriptors already known.

16. A method according to claim 12, wherein a regression calculation is carried out to correlate the descriptors with the partition parameters of the odorants.

17. A method according to claim 1, wherein a prediction is made for the partition parameters of odorants.

18. A method according to claim 1, wherein the prediction of the partition parameters of odorants is used for the composition of perfume oils and odorant mixtures.

19. A method according to claim 1, wherein perfumed products are consumer products.

20. A method according to claim 1, wherein perfumed products are detergents, care compositions, air fresheners and cleaners for industrial use.

21. A method according to claim 1, wherein perfumed products are detergents, care compositions, air fresheners and cleaners in the domestic sector.

22. A method according to claim 1, wherein perfumed products are detergents, care compositions, air fresheners and cleaners for veterinary use.

23. A method according to claim 1, wherein perfumed products are detergents, care compositions, air fresheners and cleaners in body hygiene.

24. A method of selecting an odorant or two or more odorants for the preparation of a perfume oil, comprising the following steps in sequence
    (a) in a first step for one group of odorants, determining a parameter from the relative concentration of an odorant in the phase to be perfumed relative to the concentration in the perfumed phase;
    (b) determining the descriptors of odorants using a mathematical method;
    (c) imputing the parameters determined in step (a) into a determination model and carrying out a regression calculation;

(d) making a prediction for all calculated odorants based on the regression calculation; and (e) using the odorants most effective according to the prediction in the composition of a perfume oil.

25. A method according to claim 24, wherein the determination of the relative distribution of odorants is carried out by analysis of the concentration in the perfumed phase and the phase to be perfumed.

26. A method according to claim 24, wherein the partition equilibrium between the gas phase and a liquid phase is determined.

27. A method according to claim 24, wherein the partition equilibrium between the gas phase and a solid phase is determined.

28. A method according to claim 24, wherein the partition equilibrium between a liquid phase and a solid phase is determined.

29. A method according to claim 24, wherein the partition equilibrium between the two liquid phases is determined.

30. A method according to claim 24, wherein the group of odorants comprises 2 to 200 individual compounds.

31. A method according to claim 30, wherein the group of odorants comprises 10 to 100 individual compounds.

32. A method according to claim 31, wherein the group of odorants comprises 20 to 50 individual compounds.

33. A method according to claim 24, wherein, in the calculation of the descriptors of the odorants using a mathematical method, the following steps in sequence are performed:

(a) generating conformers;

(b) optimizing the field of force;

(c) selecting the conformers by accumulation analysis;

(d) performing a semi-empirical structure optimization;

(e) selecting further conformers by accumulation analysis;

(f) optimizing the structure using ab-initio or DFT calculations; and (g) carrying out a COSMO-RS calculation.

34. A method according to claim 24, wherein a dielectric continuum calculating method is used to calculated descriptors of the odorants.

35. A method according to claim 24, wherein a mathematical determination model for the distribution between: (a) the gas phase and (b) a liquid or solid phase is described by the function $$\log P_{gas,S}^X = C_{gen}(\mu_{gas}^X - \mu_S^X) + const.$$
$$= C_{gen}\mu_{gas}^X + C_S^0 M_0^X + C_S^2 M_2^X + C_S^3 M_3^X +$$
$$C_S^4 M_4^X + C_S^{acc} M_{acc}^X + C_S^{don} M_{don}^X + const.$$

in which the symbols have the following meanings:

$P^X_{gas,S}$ represents a partition parameter between gas phase and liquid or solid phase;

$c_{gen}$ represents a general, customized preliminary factor;

$\mu^X_{gas}$ represents the chemical potential of substance X in the gas phase according to COSMO-RS;

$\mu_S^X$ represents the chemical potential of substance X in the solid or liquid phase from regression;

const represents the general regression constant;

$c_S^i$ represents the expansion coefficient of the Taylor series from regression;

acc represents the hydrogen bridge acceptor;

don represents the hydrogen bridge donor; and $M_i^X$ represents the σ-moment of the i-th order of the substance X.

36. A method according to claim 24, wherein a mathematical determination model for the distribution between: (a) a liquid or solid phase and (b) a liquid or solid phase is described by the function $$\log P_{S,S'}^X = c_{gen}(\mu_S^X - \mu_{S'}^X) + const.$$
$$= c_{S,S'}^0 M_0^X + c_{S,S'}^2 M_2^X + c_{S,S'}^3 M_3^X +$$
$$c_{S,S'}^4 M_4^X + c_{S,S'}^{acc} M_{acc}^X + c_{S,S'}^{don} M_{don}^X + const.$$

in which the symbols have the following meanings:

$p^X_{s,s'}$ represents the partition parameter between liquid phase S and liquid or solid phase S';

$c_{gen}$ represents the general, customized preliminary factor;

$\mu^X_s$ represents the chemical potential of substance X in the liquid phase S according to COSMO-RS;

$\mu^X_{s'}$ represents the chemical potential of substance X in the solid or liquid phase S' from regression;

const represents the general regression constant;

$c_S^i$ represents the expansion coefficient of the Taylor series from regression;

acc represents the hydrogen bridge acceptor;

don represents the hydrogen bridge donor; and $M_i^X$ represents the σ-moment of the i-th order of the substance X.

37. A method according to claim 36, wherein a mathematical determination model is created using the σ-moments $M_0^X$, $M_2^X$, $M_2^X$, $M_4^X$, and $M_{acc}^X$, $M_{don}^X$ and $\mu_{gas}^X$ as descriptors and a constant.

38. A method according to claim 36, wherein a mathematical determination model is created using the σ-moments $M_0^X$, $M_2^X$, $M_2^X$, $M_4^X$, and $M_{acc}^X$, $M_{don}^X$ and $\mu_{gas}^X$ as descriptors and a constant in combination with descriptors already known.

39. A method according to claim 24, wherein a regression calculation is carried out to correlate the descriptors with the partition parameters of the odorants.

40. A method according to claim 24, wherein a prediction is made for the partition parameters of odorants.

41. A method according to claim 24, wherein the prediction of the partition parameters of odorants is used for the composition of perfume oils and odorant mixtures.

* * * * *